United States Patent
Zagorsky et al.

(10) Patent No.: US 7,718,758 B2
(45) Date of Patent: May 18, 2010

(54) MIXTURES OF POLY(1,4-DIHYDROXY)-PHENYLENES (POLYHYDROQUINONES)

(75) Inventors: Andrey Leonidovich Zagorsky, St. Petersburg (RU); Karl Karlovich Kalninsh, St. Petersburg (RU); Dmitri Kirillovitsh Toporov, St. Petersburg (RU)

(73) Assignee: Andrey Zagorsky, St. Petersburg (RU)

( * ) Notice: Subject to any disclaimer, the term of this patent is extended or adjusted under 35 U.S.C. 154(b) by 0 days.

(21) Appl. No.: 12/090,649

(22) PCT Filed: Jul. 13, 2006

(86) PCT No.: PCT/RU2006/000375

§ 371 (c)(1),
(2), (4) Date: Apr. 18, 2008

(87) PCT Pub. No.: WO2007/073236

PCT Pub. Date: Jun. 28, 2007

(65) Prior Publication Data

US 2008/0275207 A1    Nov. 6, 2008

(30) Foreign Application Priority Data

Dec. 20, 2005  (RU) ............... 2005139599

(51) Int. Cl.
C08G 65/38    (2006.01)
C08G 63/00    (2006.01)

(52) U.S. Cl. ............. 528/219; 422/135; 422/136; 528/212

(58) Field of Classification Search ......... 422/135, 422/136; 528/212, 219
See application file for complete search history.

(56) References Cited

U.S. PATENT DOCUMENTS 3,257,357 A   6/1966   Stamatoff
4,396,757 A   8/1983   Ragimov et al.

FOREIGN PATENT DOCUMENTS

| DE | 4314521 | * | 10/1994 |
| EP | 379204 | * | 7/1990 |
| SU | 440 387 | | 2/1975 |
| SU | 440387 | * | 2/1975 |
| SU | 401 166 | | 1/1979 |
| SU | 401166 | * | 1/1979 |
| SU | 2 105 000 | | 2/1998 |
| SU | 2 175 317 | | 10/2001 |

| WO | 02/055047 | 7/2002 |

OTHER PUBLICATIONS

Wang et al: "Multienzymic Synthesis of Poly(hydroquinone) for Use as a Redox Polymer", Journal of the American Chemical Society, vol. 117, 1995, pp. 12885-12886.
Wang et al: "Enzymatically Prepared Poly(hydroquinone) as a Mediator for Amperometric Glucose Sensors", Polymer, Elsevier Science Publishers B.V., GB, vol. 39, No. 1 Jan. 1998, pp. 123-127.
Underwood et al: "Catalytic Oxidations in Aqueous Solution. III. Oxidation of Anthracene, Hydroquinone and Substituted Hydroquinones", Journal of the American Chemical Society, vol. 58, 1936, pp. 646-647.
A. T. Lebedev. "Mass-Spectroscopy in Organic Chemistry", M.: Binom, Knowledge Laboratory, 2003, p. 498 (in Russian).
G. Determan. "Gel-Chromatography. Gel-Filtration. Gel-Permeating Chromatography. Molecular Sieves"—M.: MIR, 1970, p. 252 (in Russian).
J. E. Wertz, J. R. Bolton, "Electron Spin Resonance. Elementary Theory and Practical Applications", Ed. by McGraw-Hill Book Company, N.Y., 1972, p. 700.
D. W. Brown, A. J. Floyd and M. Sainsbury, "Organic Spectroscopy", J. Wiley and Sons Ltd., N.Y., 1988, p. 400.
Belenkiy, M. L., "Patterns of Quantitative Estimation of Pharmacological Effect", L., 1963, p. 162 (in Russian).
M.: Zao, "Handbook for Experimental (Pre-Clinical) Studies of New Pharmacological Substances", IIA Remedium Ltd., MPH RF, 2000 (in Russian).
International Search Report from corresponding International Application No. PCT/RU2006/000375 mailed Feb. 20, 2007.

* cited by examiner

Primary Examiner—Terressa M Boykin
(74) Attorney, Agent, or Firm—Renner, Otto, Boisselle & Sklar, LLP (57) ABSTRACT

Poly(1,4-dihydroxy)-phenylenes (polyhydroquinones) having antihypoxic and antioxidative properties and prolonged paramagnetism, and represented by general formula:

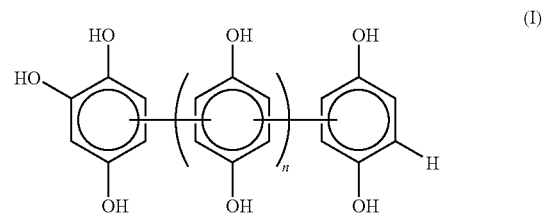

where n=0-13. The polyhydroquinones possess the possibility to increase significantly the labour-efficiency of an organism. The polyhydroquinones can be produced by hydrolysis of arbutin containing vegetable raw material followed by its polymerization; by polymerization of hydroquinone in the presence of catalyst (and without it); or by reduction of hydroquinone followed by polymerization along with purification.

7 Claims, 4 Drawing Sheets

MIXTURES OF POLY(1,4-DIHYDROXY)-PHENYLENES (POLYHYDROQUINONES)

The present invention relates to chemistry, particularly to physical chemistry of polymers, to biology and medicine, and concerns substances useful as antihypoxants, anti-oxidants, labour-efficiency improving agents found its application in pharmacology, cosmetology, food industry, veterinary medicine and other adjoining fields. The invention represents a substance synthesized from vegetable raw materials and relates to aromatic compounds, particularly to hydroquinones, and is a cyclolinear oligomer.

The most prospected application of the invention is in increase of organism defenses, in prevention and treatment of pathologic processes of cardiovascular, locomotor, immune and nervous systems accompanied by hypoxia, slow chronic diseases, under pancreatic diabetes, diseases of skin and hemopoietic organs, for treating and erasing of post-alcoholic intoxication including in chronic alcoholism, and also as a basis or component of agents being able to increase the labour-efficiency and metabolic-reduction processes of the subjects forced to endure high and intensive training and working loads, e.g. rescuers, sportsmen, astronauts.

Owing to its wide range of pharmacological activity, the invention generally can be efficiently used as a sanitary, medicinal, medical-preventive agent in strengthening, antihypoxic, antioxidative, actoprotective, detoxic, immune-protecting, dermal-tonic, and antimicrobial actions.

Known are substances based on biologically active complex of synthetic origin, some of which substances could be selected as those pertaining to aromatic compounds, particularly phenols, and being cyclolinear low molecular weight polymers exhibiting both antioxidative and antihypoxic actions.

Known is the substance similar in its structure with the proposed invention, namely polyphenylene ethers used as raw materials in manufacturing, e.g., heat-resistant films (fibers, yarns, and other molded and pressed forms of the ethers) [1]. The essential disadvantage of this substance is in its high degree of flammability during the synthesizing process, and its insolubility in aqueous media.

Known is the substance having antioxidative and antihypoxic activity and being similar in its structure to the cyclolinear oligomer, namely poly(2,5-dihydroxyphenylene)-4-thiosulphonic acid sodium salt possessing the possibility to affect a cell metabolism [2]. The known substance can be obtained by reaction between p-benzoquinone and sodium thiosulphate at the molar ratio from 10:1 to 2:1 in the aqueous-alcohol media at the temperature higher than 65° C., and the desired product is then extracted by alcohol and washed by a solvent. The polymer chain of this substance consists of hydroquinone moieties bonded each other in m-position, and a molecular weight thereof is from 352 to 784 g/mol. Disadvantages of said known substance are in that its synthesis entails a work with its initial p-benzoquinone having carcinogenic properties and high degree of toxicity.

Known is the substance having antioxidative and antihypoxic activity and being the most close in its structure to the cyclolinear oligomer, namely poly(p-dihydroxy-p-phenylene)-thiosulphonic acid sodium salt [3], selected as the closest analogue. A polymer chain of said known substance consists of hydroquinone moieties bonded in p-position. Process for manufacturing said known substance is in accomplishing the reaction of p-benzoquinone with sodium thiosulphate in aqueous media. This polymer reveals a super-oxidase dismutase activity which is proved experimentally and associated with the polymer's ability to hold efficiently unpaired electrons because of a strong interaction between phenyl rings of the polymer chain.

Technical result achieved by the present invention is in obtaining the substance which has both strongly pronounced antihypoxic and antioxidative properties and prolonged (for not less than 1 year) paramagnetic properties, simultaneously. Namely, sub-stances of the present invention are poly(1,4-dihydroxy)-phenylenes (polyhydroquinones) having antihypoxic and antioxidative properties and prolonged paramagnetism, and represented by general formula:

where n=0-13.

In parallel with the above technical result, the obtained substance possesses as well the possibility to increase significantly the labour-efficiency of organism.

The new substance can be produced by various methods: by hydrolysis of arbutin containing vegetable raw material followed by its polymerization; by polymerization of hydroquinone in the presence of catalyst (and without it); by reduction of hydroquinone followed by polymerization along with purification; etc.

This application provides two variants of this substance production.

One of them is in processing an arbutin containing vegetable raw material ground previously to slurry-like state in 20% $H_2SO_4$ in the ratio 1:1 in the mixture, which processing followed by polymerization in acid medium at 40° C. up to the boiling point of the produced mixture.

Examples of particular production of the claimed substance according to claim 1.

EXAMPLE 1

Providing 1 kg of an arbutin containing vegetable raw material ground previously to slurry-like state, processing it by 20% $H_2SO_4$ (sulfuric acid) in the ratio 1:1, and exposing it during 3 hours to polymerization at 40° C. Washing the produced material with 50% alcohol solution, drying that material at the room temperature, and then grinding it. As a result, about 30 g of black color material having about 50% of the claimed substance is produced.

EXAMPLE 2

Providing 1 kg of an arbutin containing vegetable raw material ground previously to slurry-like state, processing it by 20% $H_2SO_4$ (sulfuric acid) in the ratio 1:1, and exposing it during 3 hours to polymerization at 60° C. Washing the produced material with 50% alcohol solution, drying that material at the room temperature, and then grinding it. As a result, about 30 g of black color material having about 60% of the claimed substance is produced.

EXAMPLE 3

Providing 1 kg of an arbutin containing vegetable raw material ground previously to slurry-like state, processing it by 20% $H_2SO_4$ (sulfuric acid) in the ratio 1:1, and exposing it during 3 hours to polymerization at 90° C. Washing the produced material with 50% alcohol solution, drying that material at the room temperature, and then grinding it. As a result, about 30 g of black color material having about 50% of the claimed substance is produced. As can be seen from the adduced results of laboratory examinations, the optimal amount of the claimed substance is produced at polymerization temperature of 60° C.

The new substance can be produced as well (Claim 2) by polymerization of aqueous solution of hydroquinone, and can, at the same time, possess the same antihypoxic and antioxidative properties, prolonged paramagnetism, and possibility to increase significantly the labour-efficiency of organism.

Moreover, in this method of producing the new substance, the technical result is achieved by that the polymerization of the hydroquinone aqueous solution is carried out in acid medium at temperature from 40° C. to the boiling point of the produced solution.

In addition, the technical result is achieved by that the polymerization is carried out in the presence of catalyst.

In this case, $FeSO_4$ can be selected as the catalyst.

Examples of particular production of the claimed substance according to Claim 2.

EXAMPLE 1

Providing 1 kg of 20% hydroquinone aqueous solution, putting it into water bath, and holding it during 3 hours at 40° C. Adding 50% alcohol solution into the obtained mixture, filtering out the obtained sediment, drying it at the same temperature, and then grinding it. As a result, about 150 g of black color material having about 80% of the claimed substance is produced.

EXAMPLE 2

Providing 1 kg of 10% hydroquinone aqueous solution, putting it into water bath, and holding it during 3 hours at 40° C. Adding 50% alcohol solution into the obtained mixture, filtering out the obtained sediment, drying it at the same temperature, and then grinding it. As a result, about 150 g of black color material having about 70% of the claimed substance is produced.

EXAMPLE 3

Providing 1 kg of 30% hydroquinone aqueous solution, putting it into water bath, and holding it during 3 hours at 40° C. Adding 50% alcohol solution into the obtained mixture, filtering out the obtained sediment, drying it at the same temperature, and then grinding it. As a result, about 150 g of black color material having about 70% of the claimed substance is produced.

EXAMPLE 4

Providing 1 kg of 20% hydroquinone aqueous solution, putting it into water bath, and holding it during 3 hours at 60° C. Adding 50% alcohol solution into the obtained mixture, filtering out the obtained sediment, drying it at the same temperature, and then grinding it. As a result, about 150 g of black color material having about 90% of the claimed substance is produced.

EXAMPLE 5

Providing 1 kg of 20% hydroquinone aqueous solution, putting it into water bath, and holding it during 3 hours at 99° C. Adding 50% alcohol solution into the obtained mixture, filtering out the obtained sediment, drying it at the same temperature, and then grinding it. As a result, about 150 g of black color material having about 80% of the claimed substance is produced.

EXAMPLE 6

Providing 1 kg of 20% hydroquinone aqueous solution and adding 200 g of $H_2SO_4$ into it. Putting the obtained mixture into water bath, and holding it during 2 hours at 60° C. Adding 50% alcohol solution into the obtained mixture, filtering out the obtained sediment, drying it at the same temperature, and then grinding it. As a result, about 150 g of black color material having about 90% of the claimed substance is produced.

EXAMPLE 7

Providing 1 kg of 20% hydroquinone aqueous solution and adding 200 g of $H_2SO_4$ and 100 g of 1% solution of $FeSO_4$ into it. Putting the obtained mixture into water bath, and holding it during 1 hour at 60° C. Adding 50% alcohol solution into the obtained mixture, filtering out the obtained sediment, drying it at the same temperature, and then grinding it. As a result, about 150 g of black color material having about 90. % of the claimed substance is produced.

Figure 1:
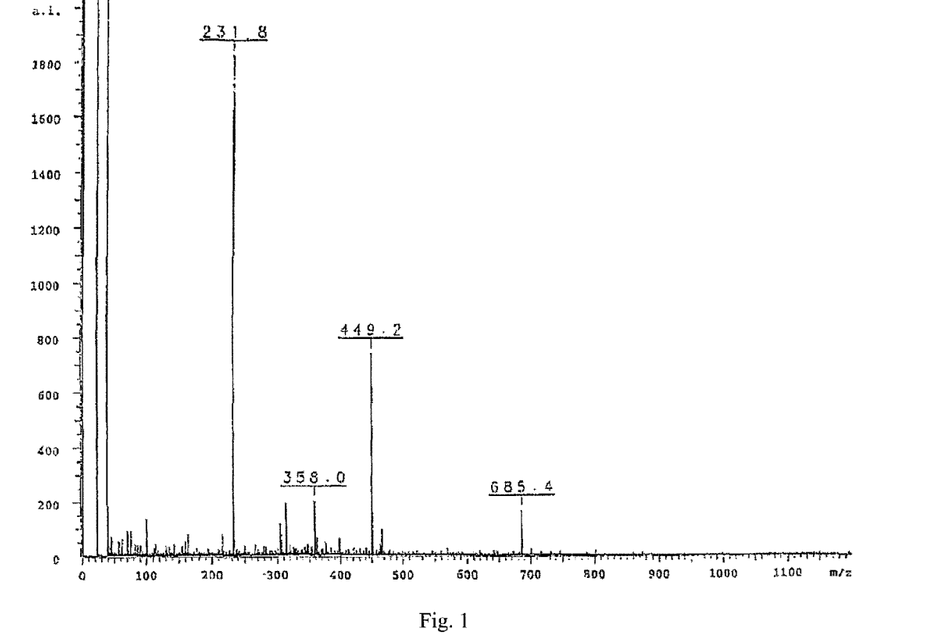
FIG. 1 is a MALDI mass spectrum of a composition prepared in accordance with an embodiment of the present invention.
Figure 2:
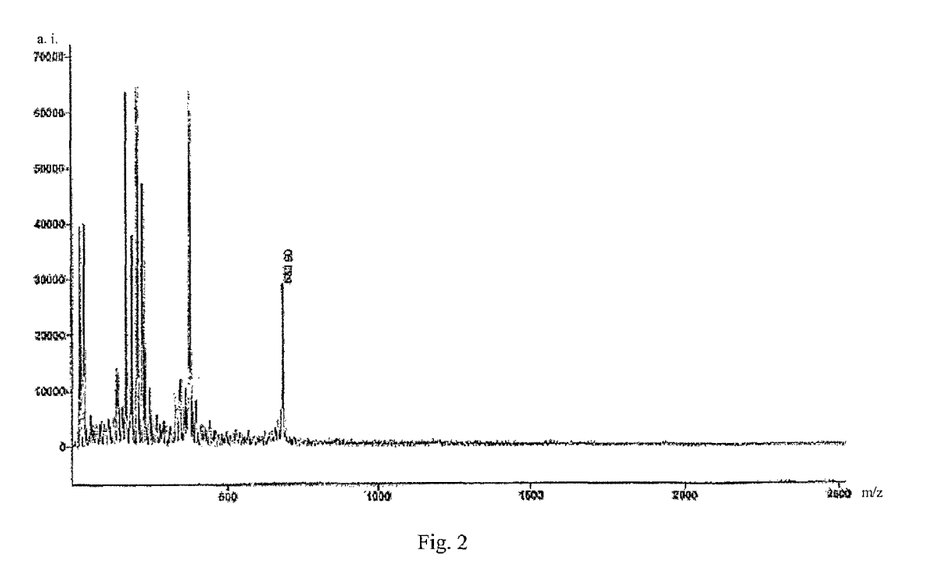
FIG. 2 is a chromatogram of a composition prepared in accordance with an embodiment of the present invention.

The claimed substance is a cyclolinear oligomer consisting of 2-15 phenyl rings of aforementioned formula, and having a molecular weight from 232 Da to 1665 Da. According to elemental analysis, gross-formula of the claimed substance is $(C_6H_6O_3)_m$. Content of carbon is 57.6 wt. %, content of hydrogen is 4.1 wt. %, content of oxygen is 38.3 wt. % (differentially measured). Molecular weight determined by MALDI (Matrix Assisted Laser Desorption Ionization) [4] mass-spectroscopy, talking into account bounded water, is: 232 Da for m=2, n=0, 450 Da for m=4, n=2, and 685 Da for m=6, n=4 (FIG. 1). Molecular weight determined by gel-permeating chromatography [5] (FIG. 2. Chromatogram of the sample made in DMF+0.05 M TFAN+0.005 M THUK using GMA Gel G-5 column) is 680 Da for m=6, n=4, and 1665 Da for m=15, n=13.

Physico-chemical constants of the substance obtained are represented in the Table 1 and illustrated by figures below.

TABLE 1

Physico-chemical constants of the obtained substance

| Colour, incl. in the solution | Specific density, g/cm³ | Solubility | | | | viscosity in DMF | Concentration of unpaired electrons (spins) | Temperature | |
|---|---|---|---|---|---|---|---|---|---|
| | | In water, g/l | in dimethylformamide (DMF) and dimethylsulfoxide (DMSO) | in acetone | in diethyl ether | | | Melting point | Decomposition point |
| Black/brown | 1.51 | 40.00 | good | poor | insoluble | 6.0 ± 0.2 | 5 × 1020 in 1 g of the substance | none | 349.79° C. |

Figure 3:
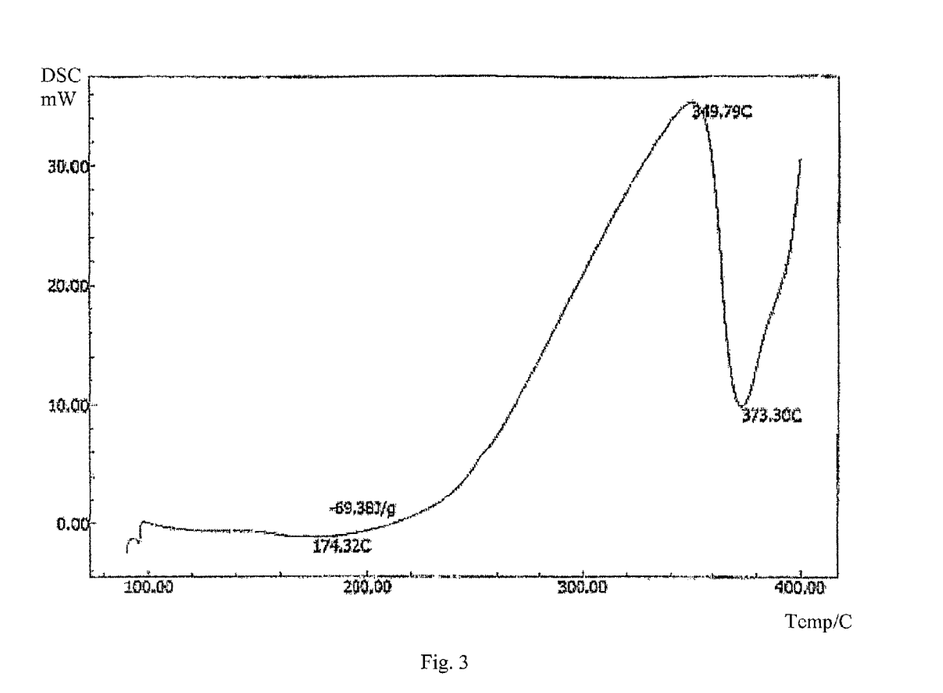
FIG. 3 is a Differential Scanning Calorimetry (DSC) curve of a composition prepared in accordance with an embodiment of the present invention.

As is clear from the physico-chemical properties listed in the Table 1, the new synthesized substance is black and turns to brown in a diluted aqueous solution; the compound has viscosity close to intrinsic viscosity of hydroquinone (5.4±0.1 g/cm³); the substance is decomposed at the temperature of 349.79° C. This temperature corresponds to the maximum of the curve shown in FIG. 3 and obtained in accordance with the thermal analysis data (differential scanning calorimetry).

Intrinsic viscosity [η] in dimethylformamide (DMF) was measured using a capillary viscometer and is 6.0±0.2 cm³/g. Said value of viscosity is similar to the one of hydroquinone (5.4±0.1 cm³/g).

Specific density of the new substance is 1.51 g/cm³. The substance has a limited solubility in polar solvents, e.g. 40 g in 1 liter of water; good solubility in DMF and DMSO; bad solubility in acetone; it is insoluble in diethyl ether and ethanol.

Figure 4:
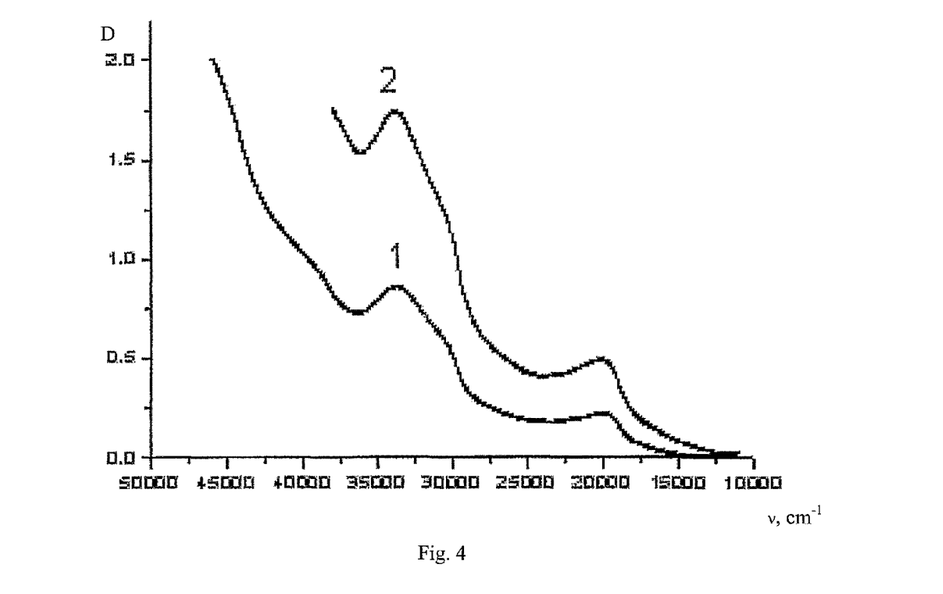
FIG. 4 is an electron absorption spectra of a composition prepared in accordance with an embodiment of the present invention.

Electronic absorption spectra of the new substance are shown in FIG. 4. Absorption band at 33600 cm⁻¹ (curve 1) in water pertains to the main substance and is analogous to the one of hydroquinone at 34600 cm⁻¹ (curve 2) related to π-π*-junction in aromatic ring. Minor component exhibiting no paramagnetic properties is represented as a ledge in area of 31000-32000 cm⁻¹ on a slope of the band 33600 cm⁻¹ of the curve 1. Distinct band of visible spectrum with the maximum 20000 cm⁻¹ (curve 1) corresponds to a stimulation of unpaired electron. The last band of the spectrum is structured and merges with a wide diffuse band extending all over the visible spectrum.

IR-spectra confirm a structure of the new substance. IR-spectroscopy analysis data are visually demonstrated in the Table 2.

TABLE 2

Characteristic frequencies in IR-absorption spectra of the new substance

| Oscillation modes and bonds 1 | Frequency range, cm⁻¹ 2 | Absorption band characteristic 3 | Reasons 4 |
|---|---|---|---|
| Stretching vibrations $v_{OH}$ of adsorbed water | 3380 | intensive band | Related with stretching vibrations of absorbed water |
| Stretching vibrations $v_{OH}$ of hydroquinone moieties | 3250 | intensive band | Relatively weak hydrogen bonds of OH-groups |
| Stretching vibrations $v_{OH}$ | 2600 | Broad band | Absorption band pertains to a very strong hydrogen bond OH—OH |
| Stretching vibrations of end-capping moieties C=O | 1730 and 1640 | Intensive band | Absorption bands pertain to stretching vibrations of end-capping moieties C=O, deformation vibrations of water, and vibrations . . . |
| Stretching vibrations $v_{C-C}$ | 1530 and 1470 | Band of average intensity | Related with stretching vibrations $v_{C-C}$ |
| Stretching vibrations $v_{C-OH}$ | 1210 | Intensive band | Related with stretching vibrations $v_{C-OH}$ |
| Non-planar deformation vibrations of C—H bonds of aromatic rings | 825 | Structured band of average intensity | Non-planar deformation vibrations of C—H bonds of aromatic rings |

Figure 5:
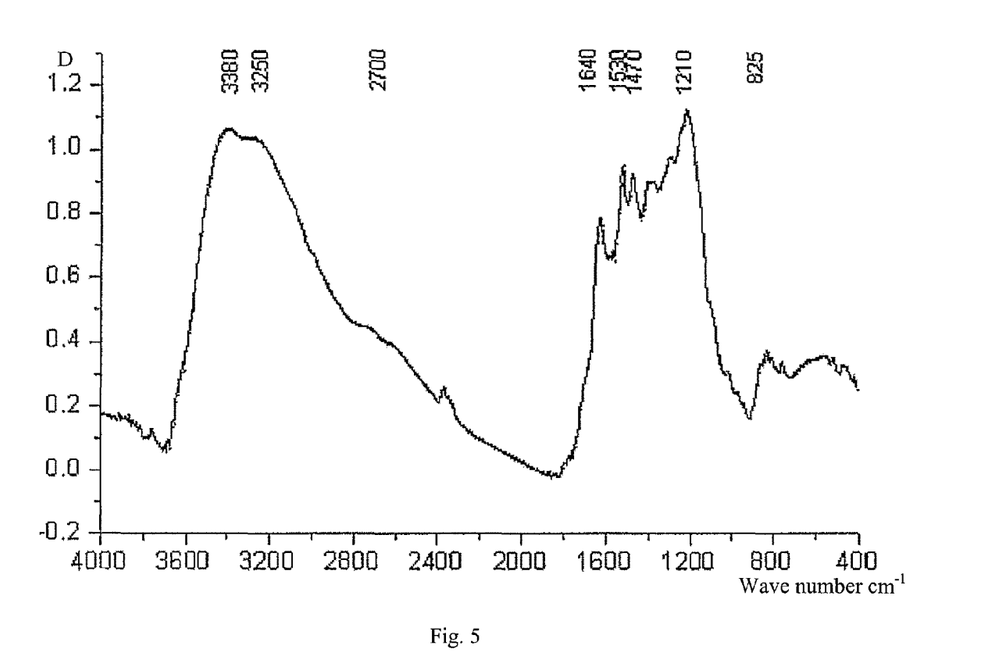
FIG. 5 is an IR spectrum of a composition prepared in accordance with an embodiment of the present invention.

As one can see from the data given in Table 2 and FIG. 5, there is an absorption band of 3380 cm⁻¹ in IR-spectra, which corresponds to stretching vibrations $V_{OH}$ of adsorbed water always contained in air-dry samples of polyhydroquinone. The band 3250 cm⁻¹ relates to stretching vibrations voH of hydroquinone moieties of the new substance, weakly bounded by hydrogen bond, while the broad band having a maximum at 2600 cm⁻¹ corresponds to very strong hydrogen bonds O—H . . . O—H between adjacent moieties of the new substance molecule. High frequency ledge at 1730 cm⁻¹ on a slope of the band 1640 cm⁻¹ related to deformation vibrations of H₂O corresponds to stretching vibrations $v_{C=O}$ of an end link. Bands 1530 cm⁻¹ and 1470 cm⁻¹ correspond to stretching vibrations $v_{C=C}$. The most intensive band in the spectrum at 1210 cm⁻¹ belongs to stretching vibrations of C—OH group of the claimed substance. The structured band at 825 cm⁻¹ corresponds to non-planar deformation vibrations of C—H bonds in aromatic rings. Pointed bands indicate the presence of mentioned structural elements in the new substance.

Analytical results confirm the presence of a polyconjugated bond system in the new substance obtained. A peculiarity of the obtained substance is in that a part of its molecules have an unpaired electron, which adds paramagnetic properties to this substance, the paramagnetism being maintained during a long time (for not less than 1 year). So, one can suppose that the obtained substance can exhibit strongly pronounced antihypoxic and antioxidative properties.

Spin concentration was measured using ESR spectrometer and a standard of known spin concentration of diphenylpicrylhydrazide (DPPH) [6]. Concentration of unpaired electrons (spins) in 1 g of the substance is $5 \times 10^{20}$, which is typical for polyconjugated systems. ESR spectra of the obtained compound are shown in FIG. 5.

Figure 6:
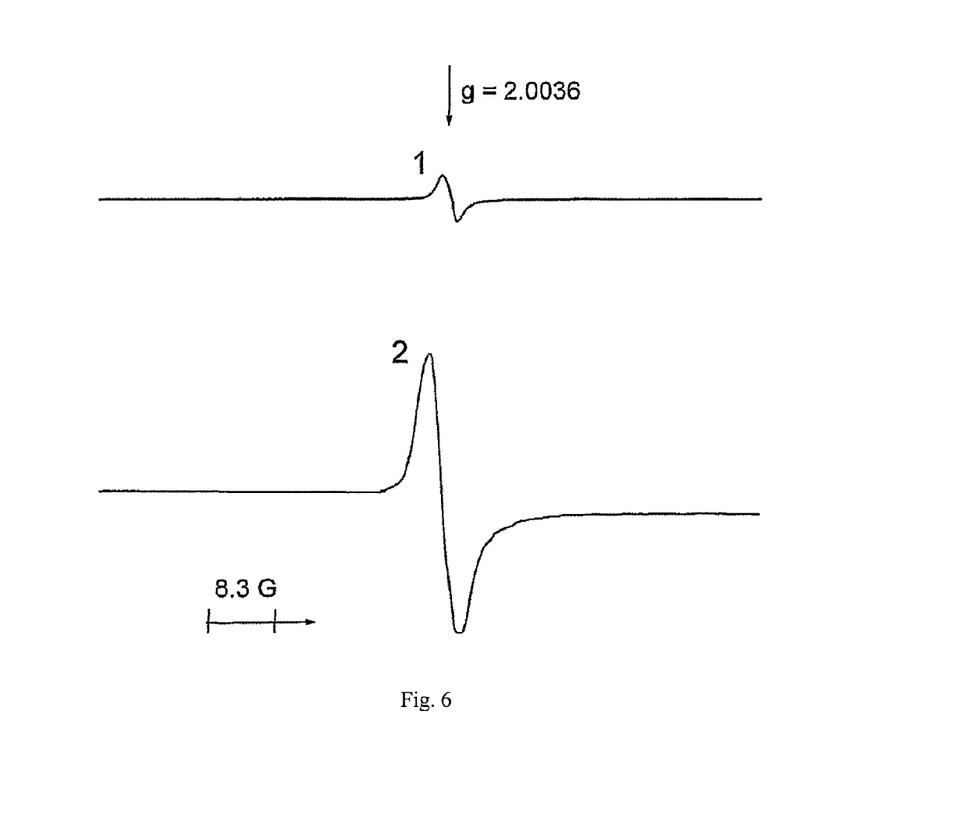
FIG. 6 is an ESR spectra of a composition prepared in accordance with an embodiment of the present invention.

The ESR spectrum in both solid and liquid (aqueous solution) forms of the claimed substance represents a single line with a linewidth of 5 Gauss without resolution of a hyperfine structure, which is indicative of the total unpaired electron delocalization and absence of its magnetic interaction with protons.

Figure 7:
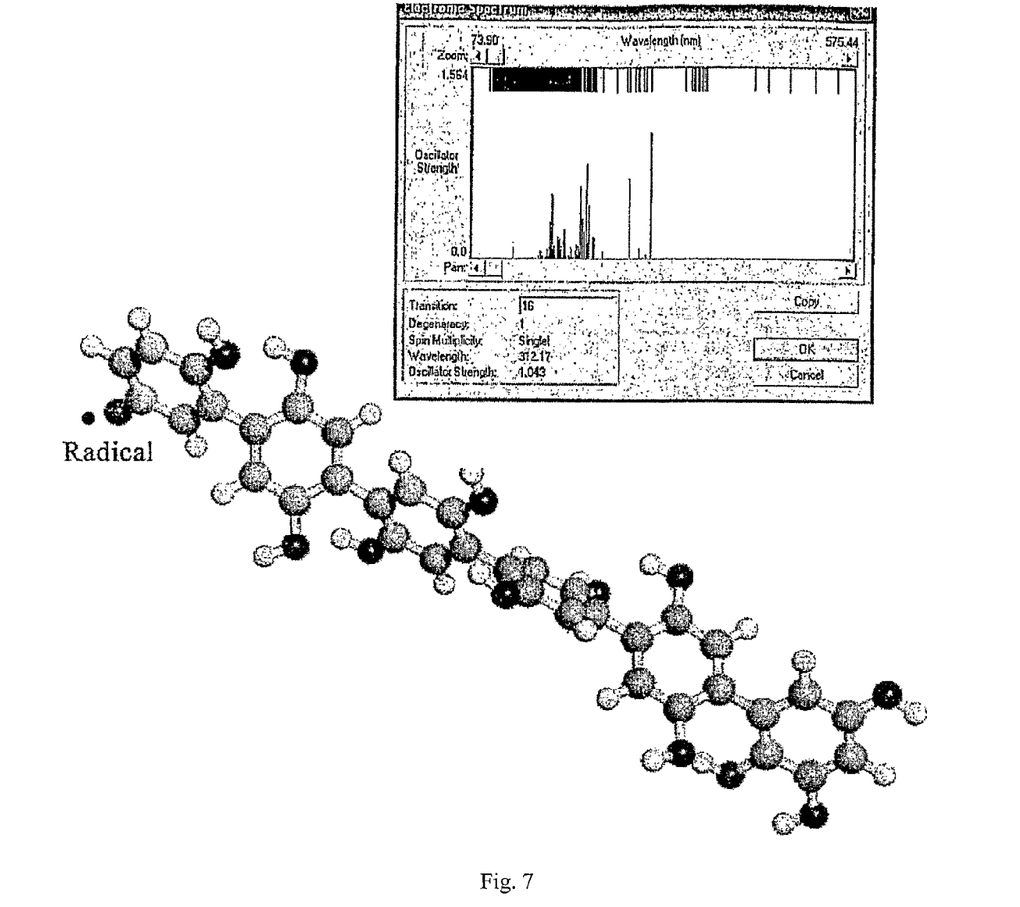
FIG. 7 shows the calculated spatial pattern of a molecule according to the present invention, which molecule has 5 hydroquinone moieties bonded with each other by carbon-carbon C—C bonds.

In order to simulate the structure of the new substance, some quantum-chemical calculations were carried out using non-empirical RHF/SBK method. FIG. 7 displays the calculated spatial pattern of a molecule of the claimed substance, which molecule consists of five hydroquinone moieties bonded with each other by carbon-carbon bond C—C. The moieties are located in para-position and turned at an angle of 47-49° from one to another, so as the effective chemical conjugation between aromatic rings along the carbon chain and system of hydrogen bonds permeating the whole molecule is occurred. Appearance of very intensive low-frequency transition in calculated absorption electron spectra of 32034 cm$^{-1}$ (f=1.04) confirms such conjugation. The analogue of this transition in experimental spectra is an intensive band near 33000 cm$^{-1}$ between TV and visible regions, which gives a dark (black) colour to the substance.

The obtained substance, poly(1,4-dihydroxy)-phenylenes (polyhydroquinones), was tested for pharmacological and biological activities (acute toxicity, antihypoxic properties, antioxidative activity, and other properties) [8,9].

Pharmacological activity of the claimed substance was compared with the known drug <<Hypoxene>> (reg. No. 001939/02-2002) having properties tested by Ministry of Public Health of Russian Federation.

For the sake of obviousness, the comparative characteristics of the new substance and drug <<Hypoxene>> are shown in the Table 3 and represented on three basic models of hypoxia in experiments on mice.

hypoxic effect. Use of the new substance, as is apparently from antihypoxic of properties (Table 3), is more effective at hypobaric hypoxia; it has a protective effect in conditions tissular and, especially, hemic hypoxia, when use of <<Hypoxene>> is not effective. Results of antihypoxic activity tests of the new substance depending on its dosage are shown in the Table 4. Drug substance of poly(1,4-dihydroxy) phenylenes (polyhydroquinones) was orally introduced (using a stomach pump) to laboratory animals. Control groups of animals were administered the equivalent volume of purified water. The sub-stance was administered in the dosage range from 100 mg/kg to 3000 mg/kg; the <<Hypoxene>> was administered in the dosage range from 100 mg/kg to 2000 mg/kg.

TABLE 4

Influence of poly(1,4-dihydroxy)phenylenes (polyhydroquinones) and <<Hypoxene>> onto antihypoxic activity in a wide range of dosages

| No. | Substance | Dosage, mg/kg | Lifetime | Lifetime growth, % | Survivability, % |
| --- | --- | --- | --- | --- | --- |
| 1 | Pure water (control sample) | 5 ml/kg | 3.88 ± 0.27 | 100 | 0 |
| 2 | <<Hypoxene>> | 31.5 | 10.80 ± 0.76 | 178.3 | 40 |
| 3 | poly(1,4-dihydroxy) phenylenes (polyhydroquinones) | 1.6 | 19.50 ± 1.34 | 402.7 | 40 |
| 4 | poly(1,4-dihydroxy) phenylenes (polyhydroquinones) | 3.2 | 15.89 ± 1.11 | 309.5 | 20 |
| 5 | poly(1,4-dihydroxy) phenylenes (polyhydroquinones) | 32 | 15.59 ± 1.09 | 301.8 | 60 |
| 6 | poly(1,4-dihydroxy) phenylenes (polyhydroquinones) | 80 | 14.66 ± 1.03 | 277.8 | 60 |
| 7 | poly(1,4-dihydroxy) phenylenes (polyhydroquinones) | 160 | 9.50 ± 0.67 | 144.8 | 40 |

As one can see from the Table 4, the test results show that the claimed substance has pronounced antihypoxic activity in a wide dosage range, and this effect has a dosage-depending non-linear nature. It is very important, that the new substance ensures more efficacy than the <<Hypoxene>>, when using in smaller dosage. Based on the analysis of obtained test results, one can also say that the invention is distinguished as well by a wider range of effective dosages.

TABLE 3

Comparison of antihypoxic properties of the new compound and known drug <<Hypoxene>> on three basic models of hypoxia

| Substance | Hypobaric hypoxia | | Tissular hypoxia | | Hemic hypoxia | |
| --- | --- | --- | --- | --- | --- | --- |
| | Lifetime growth, % | Survivability, % | Lifetime growth, % | Survivability, % | Lifetime growth, % | Survivability, % |
| <<Hypoxene>> | 178.3 | 40 | −7.7 | 0 | −25.3 | 0 |
| Poly(1,4-dihydroxy)phenylenes (polyhydroquinones) | 277.8 | 60 | 60.0 | 50 | 66.4 | 50 |

As resulted from the lifetime growth analysis carried out on three basic models of hypoxia, the new substance possesses, in contrast to the <<Hypoxene>>, the more pronounced anti- Immunotropic properties of the new substance have wider sphere, since they become apparent in conditions of immunodeficiency of different origins.

Actoprotective activity of the substance is more pronounced and becomes apparent during aerobic and aerobic-anaerobic stresses. In these cases, actoprotective effect propagates faster than using the <<Hypoxene>>. Actoprotective action of the new substance was examined using a model of consumptive physical stresses (swimming test) on laboratory animals. The results of those tests are shown in the Table 5.

TABLE 5

Actoprotective activity of poly(1,4-dihydroxy)phenylenes (polyhydroquinones) and <<Hypoxene>>

| Substances being compared | Growth of stress performing duration, % |
|---|---|
| <<Hypoxene>> | 28 |
| poly(1,4-dihydroxy)phenylenes (polyhydroquinones) | 56 |

The new substance exhibits detoxic, antiphlogistic, dermatonic and antimicrobial action, and increases ethanol tolerance. <<Hypoxene>> does not exhibit such properties. Results of performed tests have revealed one more important distinctive feature of the proposed substance in comparison with <<Hypoxene>>, its lower toxicity.

As is obvious from comparative data of performed experiments, shown in the Table 6, average lethal doses ($LD_{50}$) of the new substance is 2.5 times higher than those of <<Hypoxene>>. Histological study reveals no pathologic changes in tissues of brain, heart, lungs, liver, kidneys, stomach, pancreas, spleen, thymus, epinephros, thyroid gland of experimental animals got the substance of poly(1,4-dihydroxy)phenylenes (polyhydroquinones) in therapeutic and subtoxic doses for a long time. At the same time, some hemorrhages and pathomorphic changes in lung tissues of experimental animals were discovered after introducing the <<Hypoxene>> substance.

TABLE 6

Lethal doses $LD_{50}$ of poly(1,4-dihydroxy)phenylenes (polyhydroquinones) and <<Hypoxene>>

| Substance being compared | $LD_{50}$, M ± m, mg/kg |
|---|---|
| <<Hypoxene>> | 630.0 ± 41.0 |
| poly(1,4-dihydroxy)phenylenes (polyhydroquinones) | 1580.0 ± 31.7 |

Antioxidative properties of poly(1,4-dihydroxy)phenylenes (polyhydroquinones) were studied using a model of induced hemolysis of erythrocytes. It was found that the new substance decreased significantly the degree of membrane damage in the range of 40-80%, exceeding the action of standard antioxidant, acetic salt of tocopherol.

Results of performed studies and comparative analysis adduced in foregoing examples and tables, as well as data of experimental approbation, show that the proposed substance: possesses a unique collection of pronounced properties of antihypoxic and antioxidative activity; has low toxicity; exhibits no irritant and sensibilizing action; practically, has no contraindications. Such properties make its use especially attractive as a base or component of drugs increasing the labour-efficiency and level of metabolic-reduction processes, which are necessary for great and intensive training and working loads, particularly for sportsmen, astronauts, rescuers, persons carrying out hard physical work. The substance is also useful for manufacturing drugs having sanitary, medical-preventive, strengthening and anti-inflammatory effect.

1. U.S. Pat. No. 3,257,357.
2. RU Pat. 2,105,000, 20 Feb. 1998.
3. RU Pat. 2,175,317, 27 Oct. 2001 (closest analogue).
4. A. T. Lebedev. Mass-spectroscopy in organic chemistry,—M.: BINOM, Knowledge Laboratory, 2003, p. 493. (in Russian)
5. G. Determan. Gel-chromatography. Gel-filtration. Gel-permeating chromatography. Molecular sieves.—M.: MIR, 1970, p. 252. (in Russian)
6. Electron spin resonance. Elementary theory and practical applications. J. E. Wertz, J. R. Bolton, Ed. by McGraw-Hill Book company, N.Y., 1972, 700 p.
7. Organic spectroscopy. D. W. Brown, A. J. Floyd and M. Sainsbury. Ed. by J. Wiley and Sons Ltd., N.Y., 1988, 400 p.
8. Belenkiy M. L. Patterns of quantitative estimation of pharmacological effect.—L., 1963, 162 p. (in Russian)
9. Handbook for experimental (pre-clinical) studies of new pharmacological substances.—M.: ZAO <<IIA REMEDIUM LTD>>, MPH RF, 2000. (in Russian)

The invention claimed is:

1. A method of producing a mixture of poly(1,4-dihydroxy)-phenylenes (polyhydroquinones) having the structure where n=0-13, comprising:
  grinding an arbutin containing vegetable raw material to slurry-like state;
  mixing in 20% $H_2SO_4$ in the ratio 1:1 to form a mixture, and
  polymerizing in acid medium at 40° C. up to the boiling point of the produced mixture,
  wherein the mixture of poly(1,4-dihydroxy)-phenylenes has antihypoxic and antioxidative properties, prolonged paramagnetism, and has substantially the same infrared spectrum as that shown in FIG. 5.

2. A method of producing a mixture of poly(1,4-dihydroxy)-phenylenes (polyhydroquinones) having the structure where n=0-13, comprising:
  polymerizing an aqueous solution of hydroquinone, and
  adding a 50% alcohol solution to the polymerization product,
  wherein the mixture of poly(1,4-dihydroxy)-phenylenes has antihypoxic and antioxidative properties, prolonged paramagnetism, and has substantially the same infrared spectrum as that shown in FIG. 5.

3. The method according to claim 2, wherein the polymerization of the hydroquinone aqueous solution is carried out in acid medium at temperature from 40° C. up to the boiling point of the produced solution.

4. The method according to claim 2, wherein the polymerization is carried out in the presence of catalyst.

5. The method according to claim 4, wherein $FeSO_4$ is selected as the catalyst.

6. A method of treating hypoxia comprising administering to a patient in need thereof a therapeutically effective amount of a mixture of poly(1,4-dihydroxy)-phenylenes (polyhydroquinones) having the structure where n=0-13, and having substantially the same infrared spectrum as that shown in FIG. 5.

7. A method of increasing physical exercise performance comprising administering to a subject engaged in physical exercise an effective amount of a mixture of poly(1,4-dihydroxy)-phenylenes (polyhydroquinones) having the structure where n=0-13, and having substantially the same infrared spectrum as that shown in FIG. 5.

* * * * *